United States Patent [19]

Nelson et al.

[11] Patent Number: 5,002,652
[45] Date of Patent: Mar. 26, 1991

[54] PLASMA POLYMERIZED POLYSILOXANE MEMBRANE

[75] Inventors: Charles L. Nelson, Highland Park; Richard A. Domanik, Libertyville, both of Ill.

[73] Assignee: Abbott Laboratories, Abbott Park, Ill.

[21] Appl. No.: 205,136

[22] Filed: Jun. 10, 1988

[51] Int. Cl.$^5$ ............................................. G01N 27/40
[52] U.S. Cl. ..................................... 204/412; 204/165
[58] Field of Search ............... 204/415, 416, 418, 419, 204/435, 153.17

[56] References Cited

U.S. PATENT DOCUMENTS

| | | | |
|---|---|---|---|
| 2,913,386 | 11/1959 | Clark, Jr. | 204/195 |
| 3,070,539 | 12/1962 | Arthur et al. | 204/415 |
| 3,380,905 | 11/1968 | Clark, Jr. | 204/195 |
| 3,510,421 | 5/1970 | Gealt | 204/415 |
| 3,539,455 | 11/1970 | Clark, Jr. | 204/1 |
| 3,767,553 | 10/1973 | Bronn et al. | 204/418 |
| 4,169,779 | 10/1979 | Tataria et al. | 204/415 |
| 4,236,987 | 12/1980 | Schindler et al. | 204/418 |
| 4,269,682 | 5/1981 | Yano et al. | 204/418 |
| 4,390,405 | 6/1983 | Hahn et al. | |
| 4,634,501 | 1/1987 | LeBlanc | 204/418 |
| 4,655,880 | 4/1987 | Liu | 204/403 |

FOREIGN PATENT DOCUMENTS 2121314 12/1983 United Kingdom .

OTHER PUBLICATIONS

Stancell et al., Journal of Applied Polymer Science, 16:1505-1514 (1972).
Hahn et al., National Bureau of Standards Special Publication 415, pp. 13-17 (1975).
Tang, et al., Journal of Bioengineering, 2:381-388 (1978).
Yasuda, Applied Polymer Symposium, No. 22, pp. 241-253 (1973).
Yasuda, et al., Journal of Applied Polymer Science, 16:595-601 (1972).
Chawla, Trans. Am. Soc. Artif. Intern. Organs, 25:287-293 (1979).
Colter, et al., Biomat., Med. Dev., Art. Org. 5(1):13-24 (1977).
Murphy, et al., ISA BM 75307, pp. 31-36 (1975).
Nichols, et al., EQ 1 Enhancing Stability of Polargraphic $O_2$ Electrodes with Plasma Polymer Coatings, p. 344 (1979).
Sharma, et al., "BX 12 Plasma Polymer Coatings Applied to Oxygen Micro-Electrode," p. 287 (1979).
Tang, et al., "A Working Equation for Oxygen Sensing Disk Electrodes," pp. 9-15.
"Membrane-Covered Polarographic Detectors-Introduction and Theory," Chapter 4, pp. 59-70.

Primary Examiner—T. Tung
Attorney, Agent, or Firm—Daniel R. Curry; Priscilla E. Porembski

[57] ABSTRACT

An ultrathin selectively permeable membrane made by glow discharge plasma polymerization of a single siloxane monomer with the deposition of the polymer as a single layer upon a nonporous support material. The resulting membrane has an oxygen content between about 10% and 60% and is highly permselective. The support material can be an electrode, thereby forming an electrode that is resistant to fouling or contamination but readily accessible to oxygen.

8 Claims, No Drawings

PLASMA POLYMERIZED POLYSILOXANE MEMBRANE

BACKGROUND OF THE INVENTION

1. Technical Field

This invention relates to selectively permeable membranes and, more particularly, to polymerized silicon-containing compounds and oxygen sensing electrodes coated with such membranes.

2. Background

The use of permeable membranes for separating gases or other substances is based upon the selective permeability of certain organic materials. The terms "selective permeability" or "permselective" mean that one component will permeate through a membrane faster than other components of a mixture. The terms do not imply that the passage of one component occurs with the complete exclusion of others. Instead, they indicate that the difference in the flow rate (i.e., permeability) of two different molecular components through a membrane is based upon each component's solubility in and diffusion rate through that membrane. The mechanism results in large differences in permeation rates for the same component through different membranes as well as for different components in a given membrane.

Permselective membranes have been developed to separate and purify both liquid and gas mixtures. Permselective membranes can be used on a commercial scale for liquid-liquid or liquid-solid separation such as the conversion of sea water to fresh water. And, certain membranes can be used for gas-gas separation to obtain high purity gas. Gas permselective membranes also can be used in making oxygen sensing devices, such as oxygen electrodes.

An oxygen electrode can be used as a cathode in an oxygen sensing device for the reduction of oxygen in a sample environment. Oxygen electrodes can be used to measure the oxygen concentration of a gas or of a biological environment, such as the in vivo measurement of oxygen in blood. The electrode provides a current or voltage output which is a function of the oxygen concentration in that environment.

Conventional electrodes are constructed of conductive metals such as platinum or gold which catalyze the following cathodic reduction reaction.

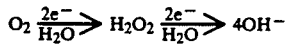

In certain environments, the electrode can rapidly lose its ability to catalyze the second step of the four electron reduction reaction. In addition, certain ions or proteins are adsorbed onto the electrode, and this fouling or contamination reduces the predictability and reproducibility of the electrode's operation. To avoid these problems, the electrodes can be protected by a permselective membrane coating.

The membrane separates the conductive metal from the environment in which it is used. The membrane's selective permeability permits oxygen to reach the electrode, so that the environmental oxygen can be measured, but prevents unwanted components from fouling the electrode.

Permeable membranes are conventionally made by dip coating and casting methods. In the casting method, an appropriate solvent is used to dissolve the membrane precursor material, and the mixture is cast onto a solid surface for drying. The solvent is removed, by heat or vacuum evaporation, leaving a membrane on the surface. The membrane then can be removed from the substrate and attached to the surface of the desired support such as an electrode. The dip method is similar, except that the substrate material is immersed in the membrane precursor material.

Problems with the dip and casting techniques occur because the permeable membrane generally is not formed on the material that will serve as the final support. Thus, the shape of the membrane may not conform identically to the support material, and typically the adhesion between the membrane and the surface of the final support material is poor. Furthermore, only materials with large surfaces are readily covered with a membrane by the casting method because the fabricated membrane must be removed from the casting surface and reapplied to the final support material. Another disadvantage is that the thickness of the membrane is difficult to control because the solvent must be evaporated from the mixture to form the membrane. Evaporation introduces variations in membrane thickness which can alter the membrane's permselective properties.

In an effort to avoid problems with adhesion, conformity, uniformity and substrate size, plasma polymerized membranes have been developed, mainly for use as reverse osmosis membranes or gas permeable membranes. Semipermeable membranes have been made using glow-discharge polymerization techniques, and such membranes have been adapted for use as electrode coatings. For example, aliphatic hydrocarbons have been plasma polymerized to form semipermeable membranes. The resultant membranes, however, do not have the highest selectivity for permeation by oxygen. Thus, such membranes are not the most satisfactory coatings for oxygen sensing electrodes. Tertiary organic silicon-containing compounds have been used together with both silicon rubber and a membranous substrate to form a semipermeable laminated membrane for use in gas-gas separations. For example, a silicon-containing compound such as silicon rubber is used to fill the pores of a porous polymeric membrane, one side of the membrane is exposed to an unpolymerizable gas plasma to cross-link the siloxane within the pores, and then a second membrane is laminated to that surface by plasma polymerization of a tertiary silicon compound. While the silicon-containing laminated membrane has a higher selectivity for oxygen than does the aliphatic hydrocarbon membrane, the process required starting with a porous membranous substrate and laminating or depositing a second membrane onto it. Because the porous membranous substrate is not formed on the material that will serve as the final support, such as an electrode, the advantages of plasma polymerization are lost, and the thickness of the final laminated membrane is controlled by the thickness of the initial porous substrate membrane.

SUMMARY OF THE INVENTION

The present invention relates to a selectively permeable single layer membrane made by glow discharge plasma polymerization of a single siloxane compound with the deposition of the resultant polymer directly upon a solid nonporous support material. The siloxane compound has the general formula:

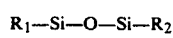

wherein $R_1$ and $R_2$ are selected from;
—$(CH_3)_3$,
—O—$(CH_2)_n$—$CH_3$ where n=0 to 5,
—$CH_2$—$C_6H_5$,
—$C_6H_5$,
—$(CH_2)_n$—COOH where n=0 to 5,
—CO—$(CH_2)_n$—$CH_3$ where n=0 to 5, and
—$(CH_2)_n$—$CH_3$ where n=0 to 5.
The resulting membrane has an oxygen content between about 10% and 60% and is highly permselective. The support material can be an electrode, thereby forming an electrode that is resistant to fouling or contamination but readily accessible to oxygen.

Plasma polymerization of the above siloxane compounds directly onto an electrode produces an electrode with a protective membrane coating having high adhesion, conformity, and uniformity. In addition, by directly applying a single silicon-containing compound via the plasma polymerization process an ultrathin permselective membrane can be formed upon the support material. Electrodes can be made wherein the permselective membrane coating has a thickness of less than one micron. Furthermore, the plasma polymerization process allows the coating of very small materials, thereby making it possible to form microminiature oxygen measuring electrodes as well as other permselective membrane-coated sensing devices.

DESCRIPTION OF THE INVENTION

The present invention is based on the discovery that a vapor of an organic siloxane compound can be used to produce an ultrathin membrane coating on a nonporous solid support material via glow-discharge plasma polymerization. The invention yields ultrathin polymeric membranes.

With the glow-discharge plasma polymerization process, a continuous ultrathin membrane of uniform thickness can be deposited on a surface of a nonporous substrate or support material without altering the overall surface topography of the support material. A single layer, semipermeable membrane can be deposited upon a material of virtually any geometry that has an unbroken, although not necessarily smooth, surface. In this process, a gaseous or vaporized membrane precursor compound is introduced into a reaction chamber at a very low pressure. Next, a plasma is generated by energizing the membrane precursor within the reaction chamber. The result is an ultrathin adherent coating of polymer deposited over the entire surface of any substrate material placed within the reaction chamber. The plasma polymerized membranes have no discernible repeating units and generally form highly crosslinked networks even though a monomer is used as the starting material.

There are several advantages to membrane production by the plasma polymerization process. First, by fabricating the membrane on the surface of the final substrate material, the problems of conformity and adhesion are virtually eliminated. The membrane adheres to the substrate/support for a considerably greater period of time than does a conventionally produced membrane. In addition, because the membrane is produced in a partial vacuum, and because the substrate can be cleaned in the reaction chamber with high purity argon, impurities that result in membrane fractures, discontinuities or distortion of transport properties typically are not incorporated into the membrane during fabrication.

It also is possible to make extremely thin membrane deposits on support materials via plasma polymerization. A uniform membrane having a thickness as low as 100 Å can be deposited upon devices such as electrodes which require an ultrathin membrane coating. The thickness of the membrane is controlled by the selection of the polymerizable starting material as well as the selection of the reaction conditions, such as the time period for which the monomer is supplied, the low rate of the supply, the frequency at which the reaction is performed, and so forth. This control also results in superior transport properties.

The single layer semipermeable membranes of the present invention use both size exclusion and diffusion rate as molecular selection processes. Small molecules can move through the interstitial voids, where as large molecules cannot. The diffusion rate is a function of the composition, molecular weight, solubility, and to some extent the concentration of the molecules in the polymer membrane. In particular, the atomic composition of the membrane greatly affects the solubility of various molecular species in the membrane, and thereby affects the transfer of those molecular species through the membrane.

The membranes of the present invention are formed from siloxane compounds, i.e., hydrocarbons bonded together by silicon-oxygen-silicon subunits. These membrane precursors are of the family of compounds with the general structural formula:

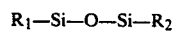

$$R_1—Si—O—Si—R_2$$

wherein $R_1$ and $R_2$ are hydrocarbon moieties of similar, identical, or dissimilar structure. The $R_1$ and $R_2$ groups include:
—$(CH_3)_3$,
—O—$(CH_2)_n$—$CH_3$ where n=0 to 5,
—$CH_2$—$C_6H_5$,
—$C_6H_5$,
—$(CH_2)_n$—COOH where n=0 to 5,
—CO—$(CH_2)_n$—$CH_3$ where n=0 to 5, or
—$(CH_2)_n$—$CH_3$ where n=0 to 5.

Membranes formed from the siloxane compounds are highly permselective to oxygen. The starting material or membrane precursor, in the present invention, is a siloxane monomer that is used to produce a plasma polymerized single layer membrane through which oxygen and small oxygen containing compounds can readily pass.

In the present invention, plasma polymerization is performed under a partial vacuum. The typical operating pressures range from about 0.1 Torr to about 10 Torr. The membrane precursor is typically reacted in its pure state using an unpolymerizable inert gas. Often, argon is used as the inert diluent or carrier gas which aids in the polymerization of the precursor. Other gases which can be used include, but are not limited to, oxygen, helium, nitrogen, neon, xenon, nitrous oxide and ammonia. The membrane precursor should have a sufficient vapor pressure such that it will vaporize in a moderate vacuum (e.g., 50 to 300 mTorr). In addition, either the precursor should contain, or the reaction conditions allow for, an appropriate percentage of oxygen (e.g., 10 to 20%) to be added to the reaction so that the membrane in its final form contains at least 10 to 20% oxygen.

The plasma polymerization process is initiated and perpetuated by means of an electric field. The primary reason for utilizing the electric field is to achieve the breakdown of the membrane precursor within the reaction chamber. When breakdown occurs, ions and reactive species are formed that initiate and perpetuate the atomic and molecular reactions that result in the formation of thin films. These ions and molecular fragments form the unique atomic and structural characteristics of the resultant polymeric membrane.

Glow discharge plasma polymerized membranes can be deposited using a number of different electrical field configurations and reaction parameters. Internal excitation, external excitation, and guided wave excitation all can initiate and perpetuate the glow discharge plasma. Inductive coupling or capacitive coupling also can be used, although these methods produce plasma discharges with different characteristics.

A typical reaction sequence begins by loading the support material to be coated into a glow discharge reaction chamber. The chamber is then evacuated to its base pressure. The base pressure is defined as the lowest pressure obtained after sustained evacuation of the chamber and is predominantly a function of the vacuum pump used. Once the base pressure is achieved, either the plasma polymerization reaction or a pretreatment reaction can be started.

A pretreatment reaction can be used to clean the surface of the support material by briefly subjecting it to an inert gas such as argon or nitrogen sputtering in the plasma. This reaction can be used to clean the surface and/or to promote adhesion of the plasma polymer film to the support material.

After cleaning the substrate material, the system is brought back to base pressure. The vaporous membrane precursor monomer is then injected into the reaction chamber and the glow discharge is initiated. By the collision of the monomer with the ions and electrons of the plasma within the reaction chamber, polymerization of the monomer occurs. The composition of the vaporous monomer need not be pure. Mixtures of inert gases or reactive gases, such as oxygen, can be used for this reaction. The resulting polymer is deposited on all exposed surfaces within the reaction chamber. If certain areas of the substrate material are not to be coated, they can be masked prior to the reaction.

The properties of the film are not only a function of the monomer structure, but also a function of the discharge frequency, power, monomer flow rate and pressure. The porosity, surface morphology, and permeability greatly vary with changes in reaction conditions. For example, a continuous thin film deposited from a 20 kHz discharge has a smooth surface morphology and a preponderance of silicon-carbon bonding. Under similar conditions of flowrate, pressure and power, a film with columnar crystalline growth and predominantly composed of $SiO_2$ is formed at a frequency of 13.56 MHz. The reaction conditions must be precisely controlled to reproduce membrane composition.

An important variable in the glow discharge plasma polymerization reaction, especially when coating microminiature support materials, is the deposition rate of the polymer. This variable can be monitored in the reaction chamber by an oscillating crystal monitor. The oscillating crystal monitor detects and displays the rate of increase of film thickness and the total film thickness. This is necessary because an advantage of the membranes of the present invention is their fast response times. The response time is the time required to sense through the membrane a change in the environment on one side of the membrane, and it is a function of thickness of the membrane, i.e., the thinner the membrane the shorter the response time. The deposition rate should not be less than 0.5 Å/sec and should not exceed 2.0 Å/sec. The deposition rate is controlled by varying the monomer flow rate. The deposition process ends when the thickness of the deposited material is about 0.5–0.8 microns.

The resulting polymer membrane is capable of serving as a semipermeable membrane for small molecules such as oxygen. The membrane can be used as a coating for many support materials including metallic, semimetallic, polymeric, or semiconductor materials. When incorporated into certain devices, such as electrodes, electrochemical methods can be used to sense these small molecules.

An oxygen sensor device using a three electrode design, rather than the conventional two electrodes, has been developed. The third electrode or auxilliary electrode, provides a longer operational life for the sensor and enables the use of a hydrated polymer membrane alone in place of both the semipermeable membrane and electrolyte system required by previous oxygen sensing devices. Other advantages include decreases in the problems of drift and fouling caused by protein adsorption/contamination. The three-electrode oxygen sensor also enables microminiaturization of the device using the polymeric membrane as both the electrolyte reservoir and protein/bulk solution barrier.

In using the device, a potential is set between two electrodes, a working electrode and a reference electrode. When the potential is applied, a current flows between the electrodes that is proportional to the oxygen concentration. Thus, because the function of the reference electrode is maintained without its operation as a current source or sink, the electrolyte no longer has to be highly conductive.

The plasma polymerization process and the membranes so produced can be used in any sensor device including in vivo oxygen sensors, oxygen sensors in machines using air mixtures, or diagnostic test sensors such as a glucose sensor using glucose oxidase to consume oxygen and then sensing the oxygen to determine the glucose level.

Any metal which is effective for catalyzing the cathodic reduction of oxygen can be used as the conductive member of the oxygen sensing electrode. For biological applications, the conductive member generally is made of a metal such as platinum which is compatible with the biological environment. Other metals which can be used include gold, silver, carbon, tungsten, palladium, tantalum, and iridium.

The following examples will serve to illustrate more particularly the present invention. Two different glow discharge plasma polymerization devices were evaluated for the production of ultrathin silicon-containing membranes. Several glow discharge devices are known in the art. The following brief descriptions, however, illustrate the basic devices used in the present invention to obtain permselective membranes of varying atomic composition.

The first device was a 13.56 megacycle (MHz) inductively coupled radio frequency reactor. The power supply was a 13.56 MHz radio frequency amplifier. The amplifier was coupled to an excitation coil through a matching network of tuneable capacitors. The capacitance was adjusted to vary the output impedance of the matching network because efficient power transmission from the power supply to the plasma occurs when the impedance of the plasma is equivalent to that of the output of the power supply. With this frequency, plasma polymerization required a net power input of 60 watts.

The reactor design employed an external excitation coil which transferred the electromagnetic radiation from the power supply to a low pressure gas, e.g., argon, within the reaction chamber. The pressure within the reaction chamber was controlled by a throttling valve connected to a vacuum pump. Inside the reaction chamber was an oscillating crystal deposition sensor for monitoring the membrane deposition rate.

The reactor was constructed with a tubular reaction chamber of glass that was three inches in diameter and 20 inches in length. A gas dispersion manifold connected the reaction chamber to a monomer supply reservoir. The monomer supply reservoir, a 100 milliliter round bottom flask, sat within a heated jacket to maintain the monomer as a liquid. Typically, a temperature of 40° C. provided sufficient vapor pressure. The monomer flow rate and consequently the pressure of the monomer from the supply reservoir to the dispersion manifold were controlled by a micrometering valve. An automatic throttling valve maintained the reaction pressure at a previously determined set point. The reaction pressure was about 0.200 to 0.600 Torr.

The argon and vaporous monomer were dispersed in an even distribution and flowed into the excitation zone which extended approximately the entire length of the chamber. The most intense region of excitation was between the dispersion manifold and the excitation coil, one inch from the first turn of the excitation coil. The substrates to be coated were placed in this region. The crystal monitor was placed as near as practical to the substrates.

The second reactor design included an audio frequency power supply to initiate and perpetuate the glow discharge plasma polymerization reaction. The power source was an audio frequency wave generator, and the signal from the wave generator was amplified by an audio amplifier. The amplified signal was transformed to a higher voltage by a transformer. Generally, a nine volt signal from the wave generator was amplified to 800 V.

The frequency of the electric field was 20 kilocycles. The electromagnetic radiation from the power supply was coupled to excitation electrodes via an impedance matching transformer having the same purpose as the matching network in the 13.56 MHz reactor design. The excitation electrodes were two copper or aluminum squares, four inches to a side, vertically opposite and parallel to each other within the low pressure reaction chamber. The power amplifier also was coupled to an oscillator. The amplifier increased the voltage of the oscillator such that a plasma could be sustained. The peak-to-peak voltage on the excitation electrodes was about 500 volts and the rms current was 0.2 amps.

The reaction chamber was a ten inch external diameter bell jar positioned on an aluminum base plate. Electrical connections, cooling water, monomer gas inlet, and the vacuum pump port were situated on the base plate. The substrates were placed on a rotating platen which could travel into and out of the reaction zone between the excitation plates. This technique improved the reproducibility and uniformity of the membrane deposition.

A gas inlet port was connected to the reaction chamber and to a three-way valve. The valve was connected to both an argon gas source and a liquid monomer reservoir. The monomer reservoir sat within a heated jacket and was heated to approximately 40° C. The argon gas was connected to one input of the three-way valve for cleaning purposes. The vaporous monomer was injected between the two plates, and the flow of monomer was regulated with a micrometering valve before entering the three way valve and the inlet gas line to the chamber. Glow discharge plasma polymers were formed on all articles within the reaction chamber. Again, an oscillating crystal deposition sensor was used to monitor the membrane deposition rate.

EXAMPLES

Example 1

The substrate material to be coated, an electrode, was placed within the reaction chamber of the radio frequency reactor and was kept under vacuum for four hours (at 10 mTorr). Prior to plasma polymerization, the reaction chamber was supplied with argon gas which was energized to initiate plasma formation. The substrate material was thus sputter-cleaned in an argon plasma (at 300 mTorr for 15 minutes with a flow rate of 30 cc/min). By cleaning the surface of the substrate material with inert gas sputtering in the plasma, the surface becomes etched. This treatment further promotes the adhesion of the polymeric membrane to the substrate material.

Example 2

In this example, hexamethyldisiloxane was polymerized in the radio frequency reactor by means of a radio frequency of 13.56 MHz. Approximately 100 ml of liquid hexamethyldisiloxane was poured into a 250 ml round bottom flask, i.e., monomer reservoir. The monomer was brought to 40° C. by the heat jacket.

The support material consisted of an electrode which was placed in the reaction chamber 2.54 cm from the first turn of the excitation coil nearest the sample entry port. Following the argon plasma cleaning of Example 1, the argon gas was shut off and the chamber was evacuated to 0.01 Torr. The shut-off valve at the opening of the flask was opened and the vaporous monomer flow rate adjusted to 1.0 cm$^3$/min. The pressure was maintained at 0.1 Torr. The glow discharge plasma polymerization reaction was initiated and sustained for four hours. The rate of deposition upon the electrode and the total film thickness were measured with the oscillating crystal monitor. The deposition rate was carefully monitored and was not allowed to fall below 0.5 Å/sec or to exceed 3.0 Å/sec. After the reaction and deposition were completed, the reaction chamber was brought to atmospheric pressure, and the substrate material was then removed.

Example 3

The coated electrodes, of Example 2 above, were evaluated by scanning electron micrography (SEM). From this analysis, precise measurements of the membrane thickness and surface morphology were made. The resulting single layer membranes, consisted of a thin coating of the polymer, and the total thickness of the polymeric deposits were between 1800 Å and 10,800 Å. The membrane thickness was very uniform and no pin holes were observed. The surface of the membrane was modular indicating columnar growth.

Samples of the hexamethyldisiloxane glow discharge polymer were also evaluated by electron spectroscopy for chemical analysis. This analysis technique provided information on the chemical structure and chemical composition of the polymeric deposit. The membranes were composed of the following elements:

| Element | Atomic Concentration |
|---------|----------------------|
| O       | 60.8                 |
| Si      | 25.8                 |
| C       | 12.5                 |

Analysis of the peak energies revealed the silicon was predominantly bonded to oxygen in the form of $SiO_2$. The $SiO_2$ structure is very similar to that found in silica glasses. The carbon in the film was predominantly bound to hydrogen as $-CH_2$. Small traces of C—O and C=O also were present in the structure of the carbon peak.

Example 4

In this example, hexamethyldisiloxane was polymerized by means of the second reactor device, a 20 kHz reactor. The monomer preparation was identical to that of Example 1. The reaction sequence also was identical to that in Example 2, with the following exceptions: the power level was 100 watts peak-to-peak; the samples were placed radially 90 degrees apart on the rotating platen which rotated at ten revolutions per minute.

Example 5

Samples of the coated electrodes of Example 4 were analyzed by SEM. The membrane thickness was extremely uniform and no pin holes were observed. The surface morphology was featureless and the coating filled the cracks and voids of the electrode surface.

Electron spectroscopy for chemical analysis was performed on a sample of this polymer as well. The membranes were composed of the following elements:

| Element | Atomic Concentration |
|---------|----------------------|
| O       | 28.5                 |
| Si      | 21.5                 |
| C       | 49.7                 |

Thus, a single siloxane compound can be plasma polymerized to form an ultrathin single layer membrane upon a solid nonporous support material with the resulting membrane being highly permselective for oxygen due to the membrane's high oxygen content. And, by polymerizing the silicon-containing compound and depositing the membrane directly upon the support material the advantages of membrane conformity, uniformity, and adhesion are maintained.

The concepts of the present invention are applicable to silicon-containing permselective membrane coatings for a variety of nonporous support materials or sensing devices. It will be appreciated, however, that one skilled in the art can conceive of many other support materials, sensing devices, and silicon-containing substances or mixtures, to which the present inventive concepts can be applied. The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

What is claimed is:

1. An oxygen sensing device, comprising:
   at least three electrodes, including a working electrode and a reference electrode;
   means for creating an electric potential between the working electrode and the reference electrode; and
   a permselective membrane formed upon the three electrodes by polymerizing a silicon-containing monomer directly onto the electrode;
   the silicon-containing monomer having the general formula $$R_1-Si-O-Si-R_2;$$

wherein $R_1$ and $R_2$ are selected from the group consisting of
   —$(CH_3)_3$
   —O—$(CH_2)_n$—$CH_3$, where n=0 to 5,
   —$CH_2$—$C_6H_5$,
   —$C_6H_5$,
   —$(CH_2)_n$—COOH, where n=0 to 5,
   —CO—$(CH_2)_n$—$CH_3$, where n=0 to 5, and
   —$(CH_2)_n$—$CH_3$, where n=0 to 5.

2. The oxygen sensing device of claim 1 wherein at least one of the electrodes comprises metal.

3. The oxygen sensing device of claim 2 wherein the metal is selected from the group consisting of platinum, gold, silver, tungsten, iridium, palladium, tantalum and alloys thereof.

4. The oxygen sensing device of claim 3 wherein the metal comprises platinum.

5. The oxygen sensing device of claim 1 wherein at least one of the electrodes comprises carbon.

6. The oxygen sensing device of claim 1 wherein the membrane has an oxygen content of at least 20% by weight.

7. The oxygen sensing device of claim 1 wherein the membrane has a thickness of up to about 1.0 micron.

8. The oxygen sensing device of claim 7 wherein the membrane has a thickness of about 100 Angstroms.

* * * * *